United States Patent
Seth

[11] Patent Number: 5,603,708
[45] Date of Patent: Feb. 18, 1997

[54] ROUNDED CORNER FASTENING TAB DIAPER CLOSURE

[75] Inventor: Jayshree Seth, Woodbury, Minn.

[73] Assignee: Minnesota Mining and Manufacturing Company, St. Paul, Minn.

[21] Appl. No.: 286,272

[22] Filed: Aug. 5, 1994

[51] Int. Cl.$^6$ ..................................................... A61F 13/15
[52] U.S. Cl. ............................................ 604/389; 604/391
[58] Field of Search ..................................... 604/389, 391, 604/358, 390, 385.1; 24/DIG. 11

[56] References Cited

U.S. PATENT DOCUMENTS

| | | | |
|---|---|---|---|
| 3,848,594 | 11/1974 | Buell | 128/284 |
| 3,926,190 | 12/1975 | Tritsch | 128/287 |
| 4,923,456 | 5/1990 | Proxmire | 604/391 |
| 5,312,387 | 5/1994 | Rossini et al. | 604/389 |

FOREIGN PATENT DOCUMENTS

| | | | |
|---|---|---|---|
| 0379850 | 12/1989 | European Pat. Off. | B31D 1/02 |
| 2624353 | 12/1987 | France | A41B 13/02 |
| 2185383 | 1/1987 | United Kingdom | A41B 13/02 |
| 2206506 | 5/1988 | United Kingdom | A41B 13/02 |

OTHER PUBLICATIONS

PCT International Search Report.

*Primary Examiner*—David Isabella
*Attorney, Agent, or Firm*—Gary L. Griswold; Walter N. Kirn; William J. Bond

[57] ABSTRACT

A fastening tab for a disposable diaper having a second half 3 with a maximum width y and a first half 2 with a minimum width x. Side edge portions are provided with no sharp corners. First half side edges (7 and 7') and the adjacent second half side edges (8 and 8', respectively) are inverted mirror images of each other taking the transverse line 10 which separates the two halves (2 and 3) as the plane of reflection. Using the bisecting longitudinal center line 12 as the plane of reflection a first side edge (7 and 8) is a mirror image of the opposing side edge (7' and 8'). The tape provides a maximum peel front at the distal end of the attached fastening tab providing a more secure closure and is capable of being cut from a stock roll in a repeating pattern without any waste.

16 Claims, 1 Drawing Sheet

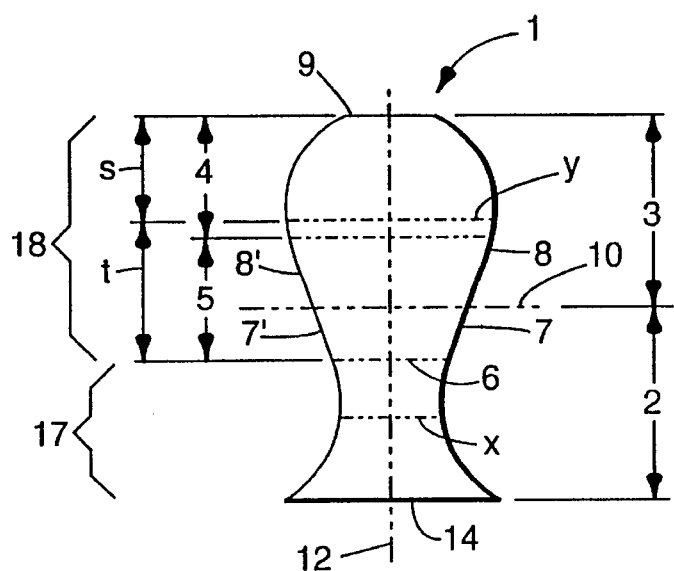
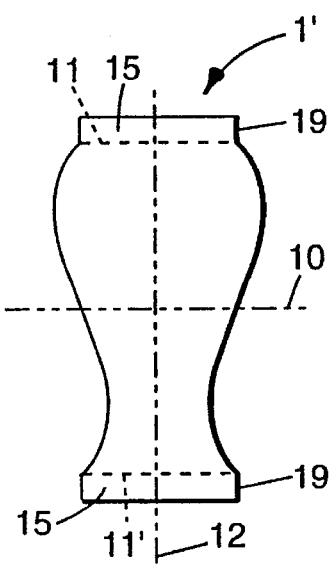
FIG.1a  FIG.1b
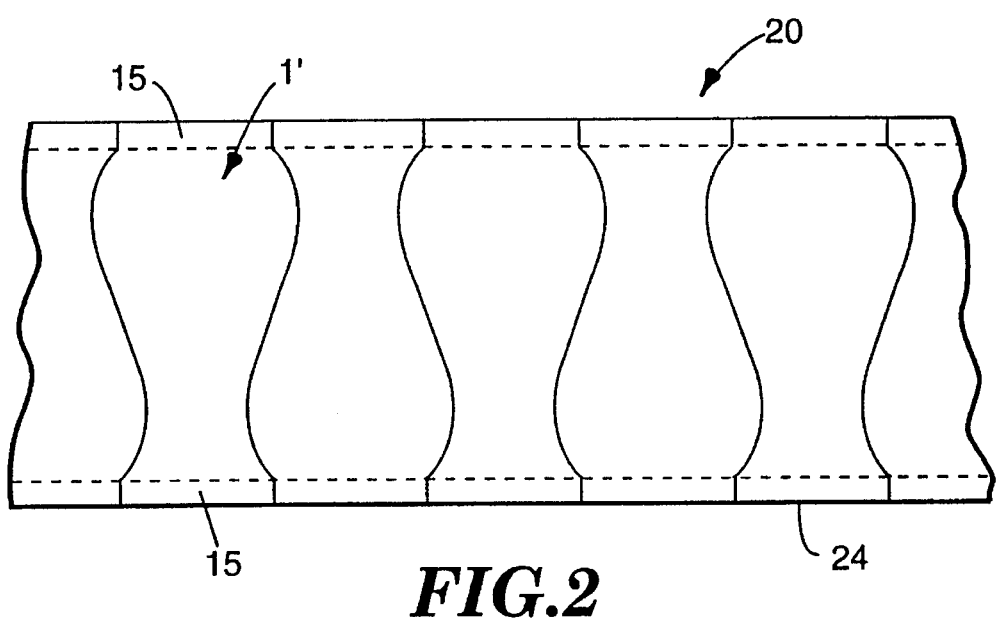
FIG.2

ROUNDED CORNER FASTENING TAB DIAPER CLOSURE

BACKGROUND AND FIELD OF THE INVENTION

The invention concerns a fastening tab for a diaper, or the like, particularly, a pressure-sensitive adhesive diaper fastening tape or mechanical fastener element.

Most conventional diaper fastening tabs are pressure-sensitive adhesive tapes or mechanical fastening elements that are rectangular in shape. This regular shape has the advantage in that it is easily converted (e.g., cut) from a stock roll or web into the individual fastening tabs and attached to the diaper, for example, as described in U.S. Pat. No. 3,848,594. However, this design is limited in terms of the fastening characteristics obtainable with a given pressure-sensitive adhesive or mechanical fastener hook and loop structure.

An alternative fastening tab design to the conventional rectangular shape is described in UK Patent Application No. 2 185 383 A. In this patent, the free end (the end attached by the user) of the diaper fastening tab tapers from its outermost peripheral end to its base, where the width is approximately that of the manufacturer's bond end of the fastening tab. A problem with this type of construction or design is that the distal end of the user-applied free end of the fastening tab can be removed at relatively low peel forces, making the tab more easily removable by the infant and increasing the potential for tab failure.

A fastening tape tab structure incorporating features of the rectangular tab and that of UK Patent Application No. 2 185 383 A is described in European Patent Application No. 379 850. In this patent application, the distal end of the diaper fastening tape tab free end is generally free of adhesive in a small tapered distal end portion of the free end tapers. The remaining user applied free end portion of the diaper fastening tape tab has a conventional rectangular shape. The advantage of the tapered adhesive-free distal end portion, of the fastening tape tab free end, is the reduction of sharp corners that children might accidentally cut themselves upon. The performance of the tape tab described in this patent would not be substantially different from that of conventional fastening tapes. Further, significant waste product would be created in the manufacture of these diaper tape tabs from a standard adhesive-coated stock roll or web.

An approach similar to that in European Patent Application No. 379 850 is described in UK Patent Application No. 2 206 506 A. A rounded end is similarly provided to protect against irritation from sharp corners to either the parent or the baby. This design would likewise have the limitations of European Patent Application No. 379 850.

Recently issued U.S. Pat. No. 5,312,387 describes a diaper fastening tab with a rectangular manufacturers bond end and a rounded free end. The rounded free end has a maximum width x-y at a distal half and a minimum width y at a proximal half. The fastening tab can be continuously cut from a roll of stock material with little or no tape waste. The design provides a maximum peel force resistance at the distal end of the fastening tape tab decreasing the potential for tape pop off. This design, although advantageous, is difficult for some diaper manufacturers to implement due to the required tape width and can provide some sharp corners on the manufacturers bond end.

There continues to be a need for improved diaper fastening tab designs from the prospective of user friendliness, performance, manufacturability and cost. The invention is directed at providing a novel fastening tab design which is advantageous in terms of all these perspectives. Particularly, the novel fastening tabs can be readily cut from a stock roll without creation of waste and provide fastening tabs with improved peel performance relative to conventional tab designs.

SUMMARY OF THE INVENTION

In accordance with the invention, a diaper fastening tab is provided having a first half, having a manufacturer's bond region, with a minimum width x and a second half, having a user's bond region, with a maximum width y, where y is greater than x. Minimum width x is at least 5 mm and the first half has a shape such that the side edge of the first half is an inverted mirror image of the directly adjacent second half side edge. This allows the fastening tab to be continuously cut as a repeating pattern from a single roll of stock material with little or no waste product. The first and second half side edges have no sharp corners, and preferably have no portion with a radius of curvature of less than 0.5 mm, between the points where the two side edges intersect the end edges or a distal end fingerlift region.

The invention tab design provides increased peel resistance at the distal end of the tab, decreasing the potential for pop off or inadvertent removal. The overall tab design provides novel fastening tab shapes in both the manufacturer's bond region and the user's bond region. These novel shapes provide improved peel performance in the users bond region over comparable rectangular conventional tabs, with the same cross-sectional area with no sharp edges or corners along the fastening tab side edges.

BRIEF DESCRIPTION OF THE DRAWINGS

FIGS. 1a and 1b are a plan views of two embodiments of a fastening tab of the present invention.

FIG. 2 is a fragmentary plan view showing the pattern from which the fastening tab of FIG. 1 is cut from a length of stock material.

DETAILED DESCRIPTION OF THE INVENTION

A diaper fastening tab of the invention 1 is shown in FIG. 1a. The fastening tab is divided into a first half 2 and a second half 3. At least a portion of the first half 2 is attached to a diaper (not shown) side edge by the manufacturers bond region, by a fastening surface 17 of conventional means, such as a pressure-sensitive adhesive, a hot-melt adhesive, sonic bonding, or the like. The second half 3 is provided with a user's bond region including a fastening surface 18, which will adhere to a suitable attachment surface on the front or frontal portion of the diaper (not shown). The fastening surface 18 on the second half 3 can be created by a suitably formulated pressure-sensitive adhesive, a mechanical fastener, or a cohesive adhesive, which is removable, from both a protective release surface (e.g., a release tape or film) and the diaper attachment surface.

The first half 2 and second half 3 are separated by an imaginary transverse line 10. In the preferred embodiment, the first half side edges (7 and 7') and the directly adjacent second half side edges (8 and 8', respectively) are inverted mirror images of each other taking the transverse line 10, which separates the two halves (2 and 3), as the plane of reflection. Further, using the bisecting longitudinal center line 12 as the plane of reflection a first side edge (7 and 8) is a mirror image of the opposing side edge (7' and 8').

The top edge 9 is a mirror image taking longitudinal center line 12 as the plane of reflection the same would be true for bottom edge 14. Preferably top edge 9 and bottom edge 14 and are parallel to each other over the major portion of their extents. In a preferred embodiment the top edge 9 joins with the two side edges at a angle of 90 degrees or more, preferably 135 degrees or more, where the angle at which the two side edges join the bottom edge plus the angle at which the two side edges join the top edge equals 180 degrees.

In another preferred arrangement, as shown in FIG. 1b, the second half 3 is provided with an adhesive-free, or other fastener-free, surface 15, Surface 15 provides a fingerlift region used to facilitate grasping of the fastening tab second half 3 by the user to remove the fastening tab user's bond region fastening surface 18 from, for example, a release tape attached to the diaper or the diaper attachment surface.

This fingerlift region 15 can be provided by leaving a terminal portion of fastening tab 1' without adhesive or other fastening means as shown in FIG. 1b. Alternatively, if the fastening surface 18 is a pressure-sensitive adhesive, terminal end portion of the second half could be folded onto fastening surface 18 to provide the fingerlift. In this case preferably the end portion folded onto itself is rectangular (i.e., the side edges join the top edge at a 90 degree angle and the side edges in this folded terminal end portion are parallel).

The overall design of the fastening tape tab described in FIGS. 1a and 1b permits easy cutting, e.g., die cutting, of multiple fastening tabs from a stock length 20 of fastening material, as shown in FIG. 2. The structure of the side edge 24 of this stock material would provide the structure of both the top and bottom edges 9 and 14, respectively.

The fastening surface 18 is provided by any suitable conventional fastening material as described above. However, if the fastening surface 18 is a pressure-sensitive adhesive, the attachment surface on the frontal portion of the diaper is preferably reinforced in some known manner to prevent tearing of the diaper backsheet when the user's bond region is removed from the diaper frontal portion. If the fastening surface 18 is a hook or loop-type material, the attachment surface on the front of the diaper must be formed from a matching hook or loop material. Any matching hook and/or loop-type material would be suitable. Similarly, with a cohesive adhesive on the fastening surface 18, the attachment surface on the frontal portion of the diaper would have to be provided with a mating cohesive adhesive surface.

Pressure-sensitive or cohesive adhesives can be solvent coated or hot-melt coated onto a backing such as a film, nonwoven web, paper, coated paper or a woven fabric to form the diaper fastening tab user's bond region fastening surface 18. The same, or different, pressure-sensitive adhesives can be used on the manufacturer's bond region fastening surface 17 for permanent attachment to a side edge region of a diaper. Mechanical fastener elements (for the fastening surface 18) can be formed directly on a fastening tab backing or applied as a separate element to the backing by suitable conventional bonding methods, such as a pressure-sensitive adhesive coating.

The second half 3 has a maximum width y, which is larger than x. This maximum width y is located between top end 9 and bisecting centerline 10, i.e., in the second half 3.

The maximum width y is preferably located at a distance s of at least 1.0 mm from the top edge 9, most preferably at least 2.0 to 5.0 mm, from top edge 9. The distance s is preferably less than t, where t is the distance from maximum width y to the transition line (or area) 6 between fastening surface 18 and fastening surface 17. If the fastening surface is divided into a distal half 4 and a proximal half 5 this relationship provides a fastening tab users bound region with a maximum peel force at a distal half 4 of the fastening surface 18 creating a more secure bond to the diaper attachment surface, when compared to a conventional fastening tab with similar surface area. With preferred embodiments, the maximum width y is at least 1.2 times x, more preferably 1.5 to 2.0 times x, with y being at least about 1 cm.

Compared to conventional rectangular fastening tab users bond regions of equivalent cross-sectional area, the fastening tab users bond regions of the invention provide improved peel force resistance at the distal half 4 of the fastening tab users bond region. The invention fastening tab also minimizes the potential for inadvertent fastening tab removal or fastening tab pop off. Once the initial peel force maximum is overcome by the parent, the remaining portion of the fastening tab can be opened at forces at, or below, those of a conventional rectangular fastening tab of equivalent users bond region surface area.

The manufacturer's bond region fastening surface 17 minimum width x is at least 5 mm preferably at least 10 mm to prevent twisting of the fastening tab when applied to the diaper. Fastening surface 17 generally is coated with a pressure-sensitive adhesive and the size of surface 17 is determined by the shape of fastening tab 1 and the location of separating line or area 6 (which generally represents the terminal edge of the diaper to which the fastening surface 17 is attached, however, fastening surface 17 can be a discrete adhesive layer or the like which terminates at line or region 6).

Top edge 9 is generally a flat edge portion with a width less than maximum width y. Further, preferably, the sum of the width of top edge 9 and bottom edge 14 equals the sum of x and y. Top edge 9 generally has a width of at least 5 mm to provide a suitable fingerlift area for a user to grip.

Side edges (7, 7', 8 and 8') have a continuous curved surface providing no sharp corners from the top edge 9 or edge 11 of fingerlift region 15 to the bottom edge 14 or the opposing edge 11'. Preferably, the minimum radius of curvature for this curved surface would be 0.5 mm. However at edges 11 and 11' a small corner can be used to provide parallel linear edge portions 19 to facilitate formation of fingerlift 15 by turning over of a terminal end portion onto adhesive coated fastening surface 18.

The entire invention fastening tab can be continuously die cut in a repeating pattern from a conventional web or stock roll with essentially no waste product, which is advantageous in terms of cost, manufacturability (it is difficult to remove small die cut waste pieces cut from a rapidly moving web) and environmental concerns.

I claim:

1. A diaper fastening tab consisting essentially of a top edge, a bottom edge and two side edges between the top edge and the bottom edge, the fastening tab between the top edge and the bottom edge consisting of a first half and a second half, the second half having a user's bond region formed of a fastening surface, for releasably attaching to a diaper attachment surface, having a maximum width y, the first half having a manufacturer's bond region formed of a second fastening surface, for permanently attaching to a diaper having a minimum width x, where y is greater than x, the second half having a shape such that, at a transverse line separating the second half from the first half, the second half side edge is an inverted mirror image of the directly adjacent first half side edge wherein the side edges of the fastening tab have curvilinear side edge portions with no sharp corners, said side edge portions extending between the top edge and the bottom edge or between the top edge or the bottom edge and a terminal fingerlift portion or between two terminal fingerlift portion(s) where the terminal fingerlift portions are located adjacent the top and/or bottom edges, said side edge portions having a minimum radius of curvature of 0.5 mm.

2. The diaper fastening tab of claim 1 wherein y is at least 1.2 times x.

3. The diaper fastening tab of claim 2 wherein x is at least 5 mm.

4. The diaper fastening tab of claim 1 wherein a top edge at the second half has a width less than y.

5. The diaper fastening tab of claim 1 wherein the second half maximum width y is at least 1.0 mm from a top edge at the second half.

6. The diaper fastening tab of claim 5 wherein the side edges of the fastening tab have side edge portions with no sharp corners from between at least one, or two, terminal fingerlift portions at the top and/or bottom edges.

7. The diaper fastening tab of claim 6 wherein said side edge portions have a minimum radius of curvature of 0.5.

8. The diaper fastening tab of claim 1 wherein the maximum width y is in a distal half of the user's bond region.

9. The diaper fastening tab of claim 7 wherein sum of the width of the bottom edge and the top edge of the fastening tab equal the sum of x plus y.

10. The diaper fastening tab of claim 1 wherein the fastening tab is a mirror image of itself on either side of a bisecting longitudinal center line.

11. The diaper fastening tab of claim 1 wherein the second half user's bond region fastening surface is a pressure-sensitive adhesive surface.

12. The diaper fastening tab of claim 1 wherein the second half user's bond region fastening surface is a mechanical fastener surface.

13. The diaper fastening tab of claim 1 wherein the second half user's bond region fastening surface is a cohesive adhesive surface.

14. The diaper fastening tab of claim 9 wherein the top edge and the side edges form an angle of at least 135 degrees.

15. The diaper fastening tab of claim 6 wherein the fingerlift portion is formed by a terminal end of the second half with no fastening surface.

16. The diaper fastening tab of claim 11 wherein the side edges and the top edge form an angle of 90 degrees and a fingerlift portion is formed by folding a rectangular portion of a terminal end of the second half onto the users bond region fastening surface.

* * * * *